(12) United States Patent
Gustafsson

(10) Patent No.: US 10,117,620 B2
(45) Date of Patent: Nov. 6, 2018

(54) SENSOR GUIDE WIRE DEVICE AND SYSTEM INCLUDING A SENSOR GUIDE WIRE DEVICE

(71) Applicant: ST. JUDE MEDICAL COORDINATION CENTER BVBA, Zaventem (BE)

(72) Inventor: Pär Gustafsson, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 0 days.

(21) Appl. No.: 14/206,696

(22) Filed: Mar. 12, 2014

(65) Prior Publication Data

US 2014/0276223 A1  Sep. 18, 2014

Related U.S. Application Data

(60) Provisional application No. 61/790,997, filed on Mar. 15, 2013.

(51) Int. Cl.
*A61B 5/00* (2006.01)
*A61B 5/0215* (2006.01)

(52) U.S. Cl.
CPC .......... *A61B 5/6851* (2013.01); *A61B 5/0215* (2013.01)

(58) Field of Classification Search
CPC ....... A61B 5/01; A61B 5/021; A61B 5/02141; A61B 5/0215; A61B 5/036; A61B 5/145; A61B 5/14503; A61B 5/6847; A61B 5/6851; A61M 2025/09183
See application file for complete search history.

(56) References Cited

U.S. PATENT DOCUMENTS

| 5,873,835 A | 2/1999 | Hastings et al. |
| 7,967,761 B2 * | 6/2011 | Smith ............... A61B 5/036 600/585 |
| 2004/0225232 A1 * | 11/2004 | Malmborg .......... A61B 5/0215 600/585 |

(Continued)

FOREIGN PATENT DOCUMENTS

| WO | WO 03/094693 A2 | 11/2003 |
| WO | WO 2012/000798 A1 | 1/2012 |

OTHER PUBLICATIONS

International Search Report dated Jul. 21, 2014, 9 pgs.

(Continued)

*Primary Examiner* — Rene Towa
(74) *Attorney, Agent, or Firm* — Foley & Lardner LLP

(57) ABSTRACT

A sensor guide wire for an intravascular measurement of a physiological variable in a living body may include a sensor element configured to measure the physiological variable based on exposure to fluid in the living body; and a cylindrical-shaped jacket forming an interior space housing the sensor element. The jacket comprises an outer circumferential wall with a circumferential surface extending between distal and proximal longitudinal ends of the jacket. The outer circumferential wall of the jacket does not include any apertures along its circumferential surface so as to prevent fluid from passing through the outer circumferential wall and/or the jacket has a constant cross section along its entire length.

22 Claims, 8 Drawing Sheets

(56) References Cited

U.S. PATENT DOCUMENTS

| | | | |
|---|---|---|---|
| 2005/0011272 A1* | 1/2005 | Tenerz | A61B 5/6851 |
| | | | 73/756 |
| 2010/0228112 A1 | 9/2010 | Von Malmborg | |
| 2011/0213220 A1 | 9/2011 | Samuelsson et al. | |
| 2012/0289808 A1 | 11/2012 | Hübinette | |

OTHER PUBLICATIONS

International Preliminary Report on Patentability issued in application No. PCT/IB2014/001104 dated Sep. 24, 2015.
Written Opinion of the International Searching Authority and International Search Report issued in application No. PCT/IB2014/001104 dated Jul. 21, 2014.

* cited by examiner

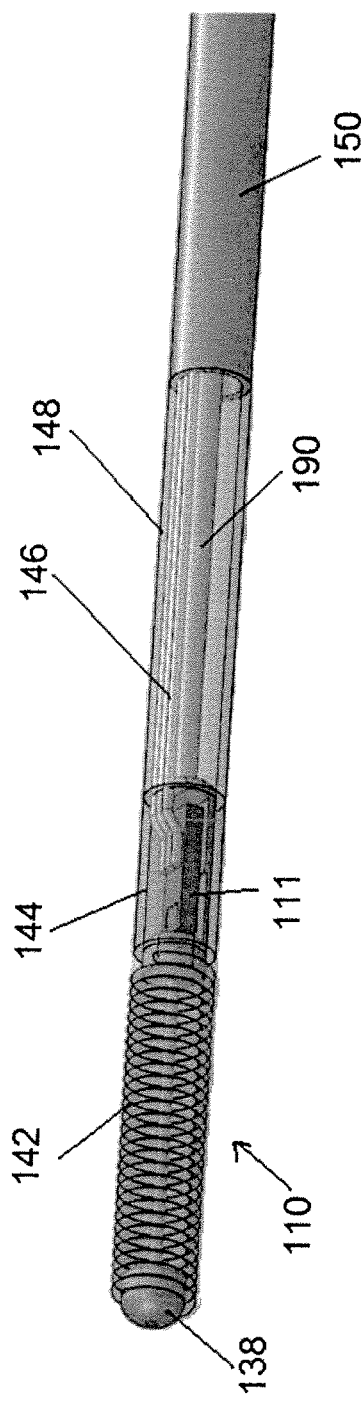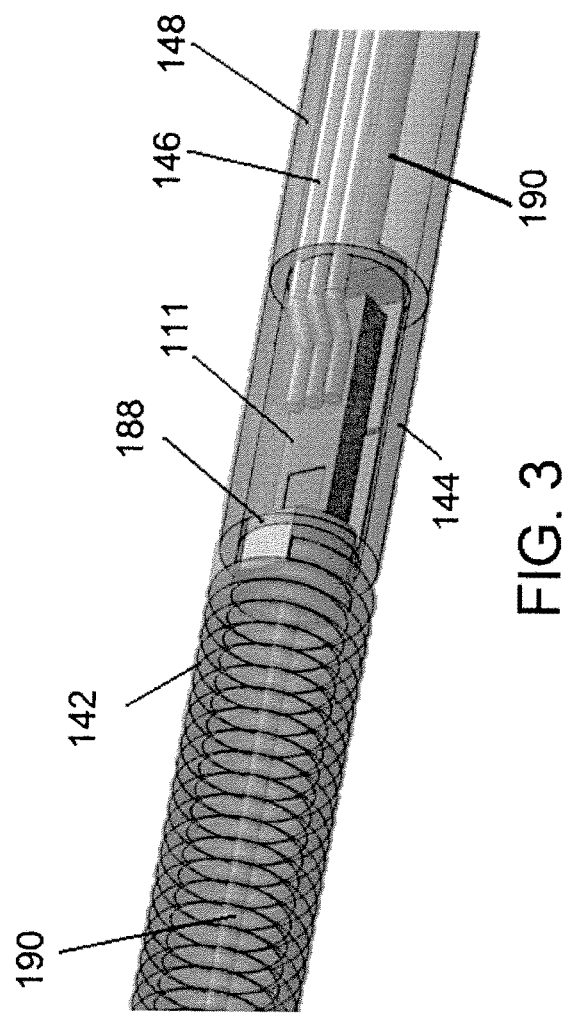

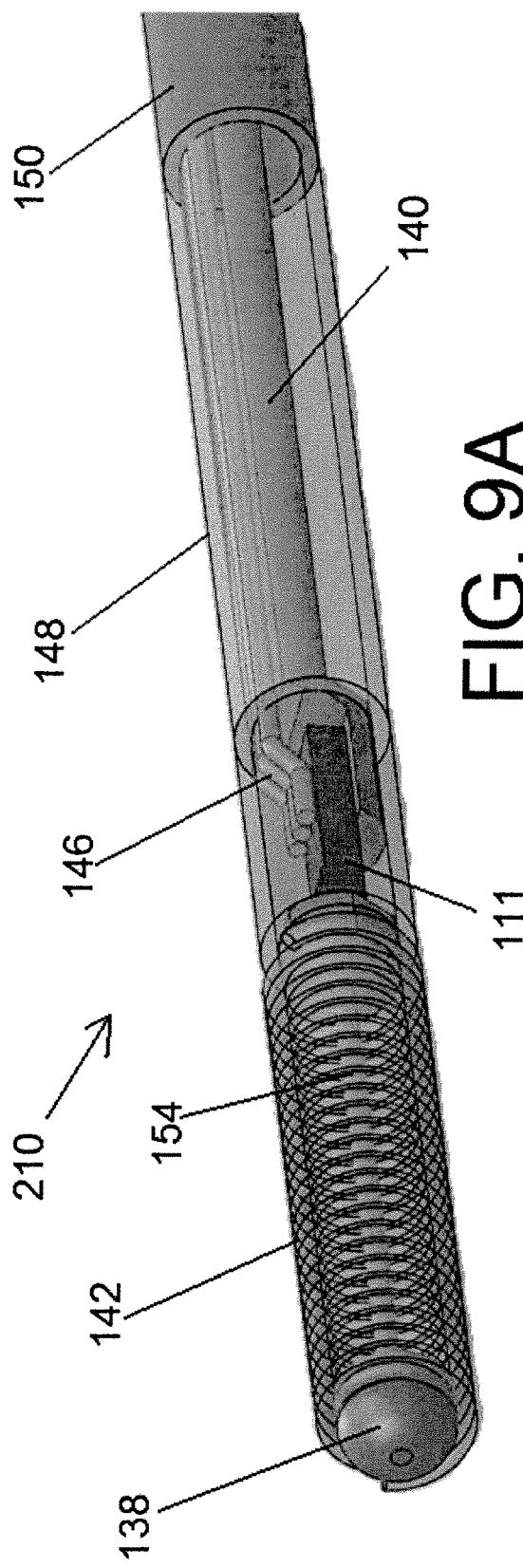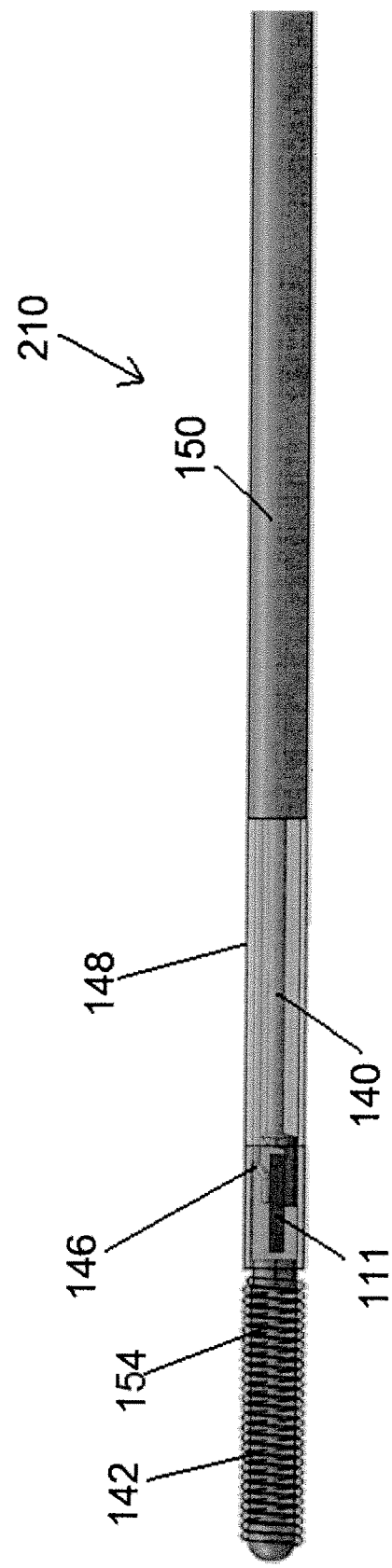

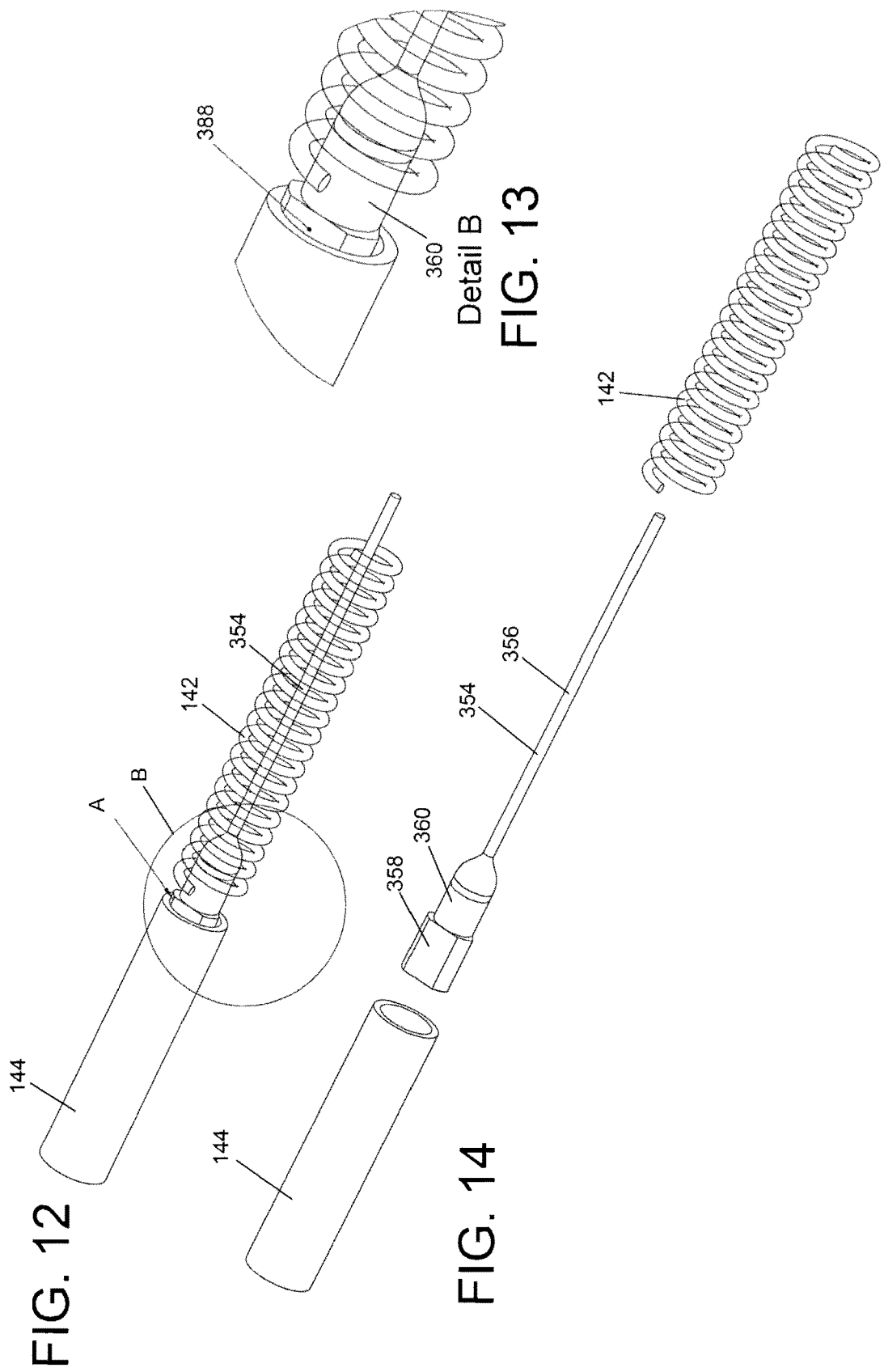

SENSOR GUIDE WIRE DEVICE AND SYSTEM INCLUDING A SENSOR GUIDE WIRE DEVICE

FIELD OF THE INVENTION

The invention generally relates to the area of medical devices. More particularly, the present invention concerns a sensor guide wire device for intravascular measurements of a physiological variable, e.g. pressure or temperature, inside a living human or animal body, and also to a system for intravascular measurements of a physiological variable in a living body.

BACKGROUND

In many medical procedures, medical personnel wish to monitor various physiological conditions that are present within a body cavity of a patient. These physiological conditions are typically physical in nature, such as, for example, pressure and temperature, and provide the physician or medical technician with information as to the status of a patient's condition. The manner by which these types of parameters are measured and monitored should be as safe, as accurate and as reliable as possible.

Equipment and processes have been developed for assisting medical personnel, such as physicians or medical technicians, in diagnosing physiological conditions of a patient. For example, sensor guide wires in which a sensor is mounted at the distal end of a guide wire have been developed. The sensor may, for example, be an intravascular pressure sensor that is arranged to measure blood pressure at various points within the vasculature to facilitate locating and determining the severity of, for example, stenosis or other disrupters of blood flow within the vessels of the living body.

SUMMARY

According to one embodiment of the present invention, a sensor guide wire for an intravascular measurement of a physiological variable in a living body may comprise: a sensor element configured to measure the physiological variable based on exposure to fluid in the living body; and a cylindrical-shaped jacket forming an interior space housing the sensor element. The jacket comprises an outer circumferential wall with a circumferential surface extending between distal and proximal longitudinal ends of the jacket. The outer circumferential wall does not include any apertures along its circumferential surface so as to prevent fluid from passing through the outer circumferential wall.

According to another embodiment of the present invention, a sensor guide wire for an intravascular measurement of a physiological variable in a living body may comprise: a sensor element configured to measure the physiological variable based on exposure to fluid in the living body; and a cylindrical-shaped jacket forming an interior space housing the sensor element. The jacket comprises an outer circumferential wall with a circumferential surface extending between distal and proximal longitudinal ends of the jacket. The jacket has a constant cross section along its entire length.

It is to be understood that both the foregoing general description and the following detailed descriptions are exemplary and explanatory only, and are not restrictive of the invention as claimed.

BRIEF DESCRIPTION OF THE DRAWINGS

The features, aspects and advantages of the present invention will become apparent from the following description, appended claims, and the accompanying exemplary embodiments shown in the drawings, which are briefly described below.

FIGS. 2A and 2B are schematic drawings showing a sensor guide wire used in the system of FIG. 1.

FIG. 3 is a schematic drawing showing a close up of the symmetrical jacket and sensor element of FIGS. 2A and 2B.

FIGS. 9A and 9B are schematic drawings showing a sensor guide wire used in the system of FIG. 1.

FIG. 12 is a partial schematic drawing showing a sensor guide wire used in the system of FIG. 1.

FIG. 13 shows a close-up of detail B from FIG. 12.

FIG. 14 shows an exploded view of the sensor guide wire components of FIG. 12.

DETAILED DESCRIPTION

Figure 1:
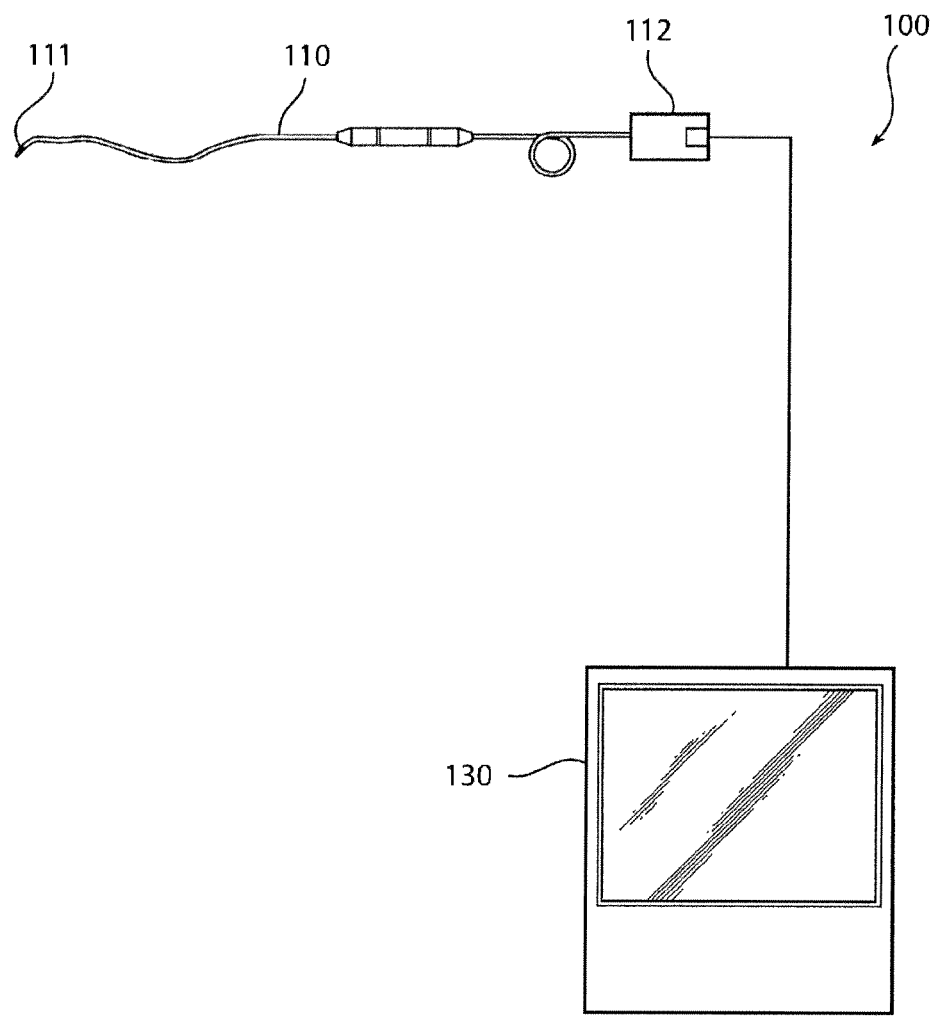
FIG. 1 is a schematic drawing showing a system for intravascular measurement according to one embodiment of the present invention.

FIG. 1 shows a system 100 comprising a sensor guide wire according to one embodiment of the present invention. The arrangement comprises a sensor guide wire 110, and a physiological monitor 130. The sensor guide wire 110 may comprise a sensor element 111 arranged at the distal end of the sensor guide wire 110. The sensor element 111 may be arranged to sense a physiological variable in a living body, such as a human or animal body, and provide a sensor signal. The sensor guide wire 110 is a disposable device which typically includes a connector 112 (which may be a female or male connector) for connection to the physiological monitor 130 which processes the sensor signal to generate a measurement of the physiological variable. Alternatively, a signal converting device or an interfacing device may be disposed between the connector 112 and the physiological monitor 130, such as for example, the signal converting and interfacing devices disclosed in U.S. Patent Application Publication No. 2012/0289808, which is hereby incorporated by reference in its entirety for their teachings related to signal converting and interfacing devices, the use of physiological monitors, and the structure and use of sensor guide wire devices. Such a signal converting or interfacing device may be arranged to interface the guide wire-mounted sensor element 111 to the physiology monitor 130 such that a signal indicative of the physiological variable sensed by the sensor element 111 is pre-processed and forwarded to the physiology monitor 130.

Figure 2B:
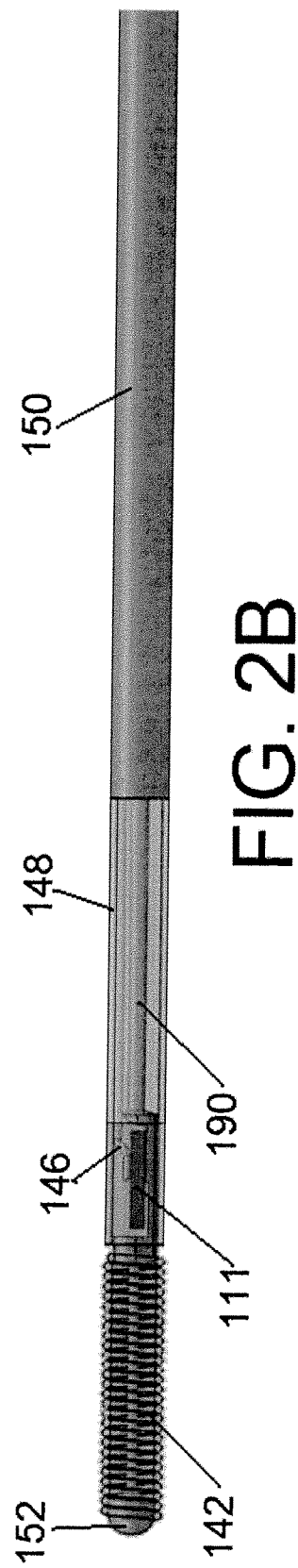

FIGS. 2A, 2B, and 3 show a sensor guide wire 110 that can be used in the system of FIG. 1. The sensor guide wire includes the sensor element 111, a distal tip 138, a core wire 190, a coil 142, a symmetrical jacket 144, one or more microcables 146, a tube section 148, and a proximal section 150. The diameter of the sensor guide wire 110 preferably varies between 0.25-2.5 mm; for use in coronary arteries, for example, the diameter is normally 0.35 mm. The distal tip 138 is the most distal portion, i.e. that portion which is going to be inserted farthest into the vessel, and the proximal section 150 is the most proximal portion, that is, that portion being situated closest to the connector 112 shown in FIG. 1.

The sensor element 111 may be used to sense any suitable physiological variable, such as, for example, pressure or temperature. The sensor may be a microchip, a pressure sensitive device in the form of a membrane, a thermistor, a sensor for measuring the concentration or presence of a blood analyte, or other suitable pressure, temperature, or other variable-measuring device. Furthermore, the sensor element 111 may be a plurality of sensor detecting devices. The physiological monitor 130 may use the sensor readings from the sensor element 111 to determine blood pressure, blood temperature, blood flow, the concentration or presence of one or more blood analytes, and/or Fractional Flow Reserve measurements (FFR). In short, FFR is used to identify constrictions of coronary vessels, for example, in the great cardiac vein, by obtaining the ratio between the pressure distally and proximally of a constriction.

The sensor element 111 is connected to the microcables 146 for transmitting signals between the sensor element 111 in the distal part of the sensor guide wire 110 and the connector 112 at the proximal end of the proximal section 150. Examples of suitable microcables are described, for example, in U.S. Patent Application Publication No. 2010/0228112, U.S. Patent Application Publication No. 2011/0213220, and U.S. Patent Application Publication No. 2012/0289808, all of which are hereby incorporated by reference in their entireties for their teachings related to microcables in guide wire assemblies and the structure and use of guide wire assemblies.

Figure 4:
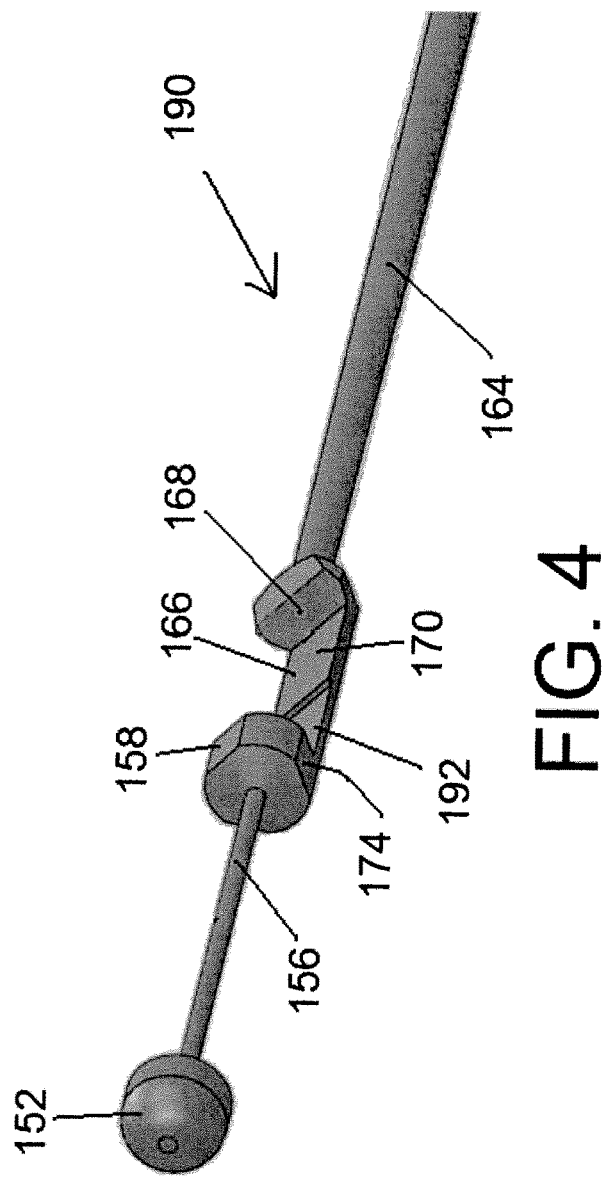
FIG. 4 shows the core wire of the sensor guide wire of FIGS. 2A and 2B.

The core wire 190 is shown in FIG. 4, and may comprise a first body portion 164, and a sensor mounting portion 166. The sensor mounting portion 166 is a first enlarged portion of the core wire 190 in which the sensor element 111 is placed on a horizontal flat portion 170 which is connected to the body portion 164 by a connecting portion 168. However, the core wire 190 may have other configurations for mounting the sensor element 111 thereon. The core wire 190 further comprises a second body portion 156 and a second enlarged portion 158 at the proximal end of the second body portion 156. The second enlarged portion 158 and the sensor mounting portion 166 on which the sensor element 111 is mounted may be connected to each other by a bridging portion 192. The first body portion 164, the sensor mounting portion 166, the connecting portion 168, the second body portion 156, the second enlarged portion 158, and the bridging portion 192 may be formed as one integral structure fashioned as a unitary one-piece structure or may be two or more distinct components that are connected to each other by suitable attaching mechanisms, for example, laser welding, adhesives, soldering, or other suitable mechanism. The core wire 190 may comprise any suitable material, such as for example, stainless steel or Nitinol (NiTi).

The distal tip 138 may comprise an arced tip 152, which is connected to the second body portion 156 of the core wire 190.

The coil 142 may be a radioopaque coil made of, for example, platinum. The coil 142 may have any suitable length, for example, between about 10 mm to about 50 mm.

Figure 5:
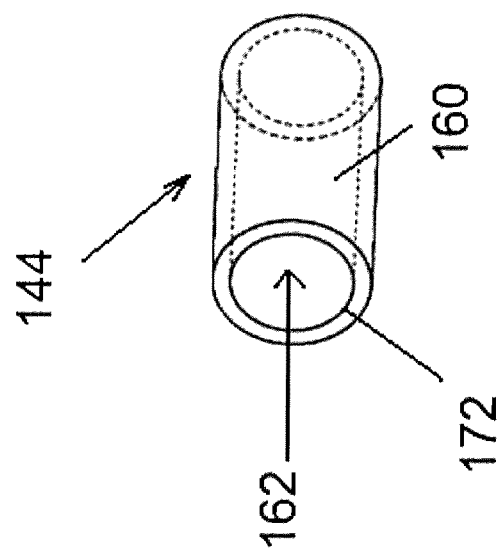
FIG. 5 shows the symmetrical jacket of FIGS. 2A and 2B.

The symmetrical jacket 144 that houses the sensor element 111 is shown in FIG. 5, and may be rotationally symmetric. The jacket 144 is cylindrical and has an outer circumferential wall 160 through which a passageway 162 runs from a distal longitudinal end to a proximal longitudinal end. The outer circumferential wall does not include any apertures along its circumferential surface so as to prevent fluid from passing through the circumferential wall. As such, the jacket has a constant cross section along its entire length. The outer diameter of the jacket 144 acts as a portion of the outer surface of the sensor guide wire. The jacket 144 may be made from any suitable material such as stainless steel or a super elastic alloy, such as Nitinol, copper-tin, copper-zinc, or copper-zinc-tin. The length of the symmetrical jacket may be within the range of about 1 mm to about 5 mm.

The tube section 148 is connected to the proximal end of the symmetrical jacket 144 and to the distal end of the proximal section 150. The tube section 148 may be made from either a hydrophilic material or made with a material coated with a hydrophilic substance. In the latter case, the material to be coated may be any suitable material such as stainless steel or a super elastic alloy, such as Nitinol, copper-tin, copper-zinc, or copper-zinc-tin.

The proximal section 150 may be made from any suitable material such as stainless steel or a super elastic alloy, such as Nitinol, copper-tin, copper-zinc, or copper-zinc-tin. The length of the proximal section 150 may be about 150 mm to about 2400 mm, preferably about 1000 mm to about 2000 mm. The connector 112 is connected on the proximal end of the proximal section 150. According to one embodiment, the proximal section 150 may be a hypo tube.

As a matter of assembly, the core wire 190 and coil 142 are joined to each other at the arced tip 152 and/or the enlarged portion 158 by, for example, laser welding, adhesives, soldering, or other suitable mechanism. The coil 142, the core wire 190, the tube section 148, or any combination thereof are joined to the jacket by, for example, laser welding, adhesives, soldering, or other suitable mechanism. The tube section 148 and the proximal section 150 are connected to each other by, for example, laser welding, adhesives, soldering, or other suitable mechanism.

The interaction between the enlarged portion 158 of the core wire 190 and the symmetrical jacket 144 will now be explained. Typically, a jacket 144 housing a sensor element does not have a completely symmetrical design because the jacket has an opening or aperture along its circumferential surface since the sensor element 111 needs exposure to the surrounding environment, such as the interior of a blood vessel or body cavity, so as to obtain readings of the physiological variable of interest, such as the blood pressure or temperature. This opening in its circumferential surface creates an asymmetry that inhibits symmetrical torque transfer and symmetrical bend radius when the sensor guide wire is inserted into the blood vessel or body cavity. Symmetrical torque transfer and symmetrical bend radius help a doctor or medical practitioner steer the sensor guide wire to a desired location in the body, for example, from an opening in the femoral artery to the heart. Removing the aperture along the jacket's circumferential surface permits more symmetrical torque transfer and symmetrical bend radius during use, makes the jacket easier to manufacture, provides more flexibility regarding the mounting of the sensor element within the jacket, and removes the sharp edges that the aperture may have. Thus, according to one embodiment of the present invention, the outer circumferential wall does not include any apertures along its circumferential surface and/or the jacket has a constant cross section along its entire length.

Figure 7:
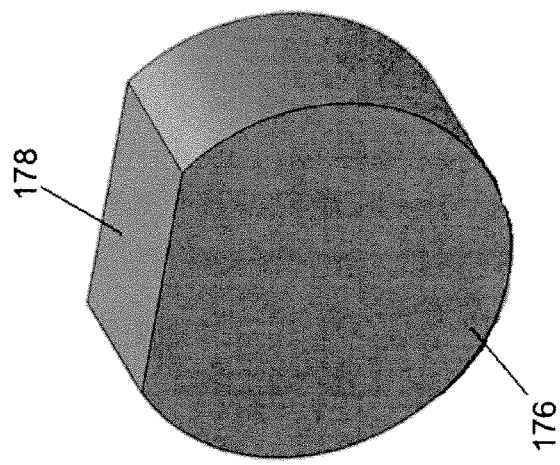
FIG. 7 shows a perspective view of the enlarged portion of the core wire of FIG. 4 according to another embodiment of the present invention.
Figure 6:
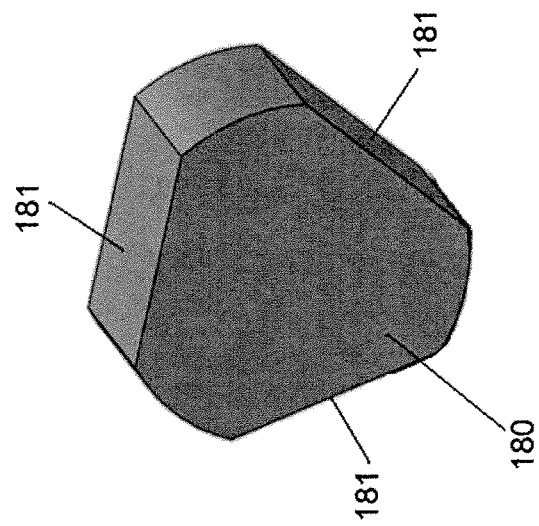
FIG. 6 shows a perspective view of the enlarged portion of the core wire of FIG. 4 according to one embodiment of the present invention.
Figure 10:
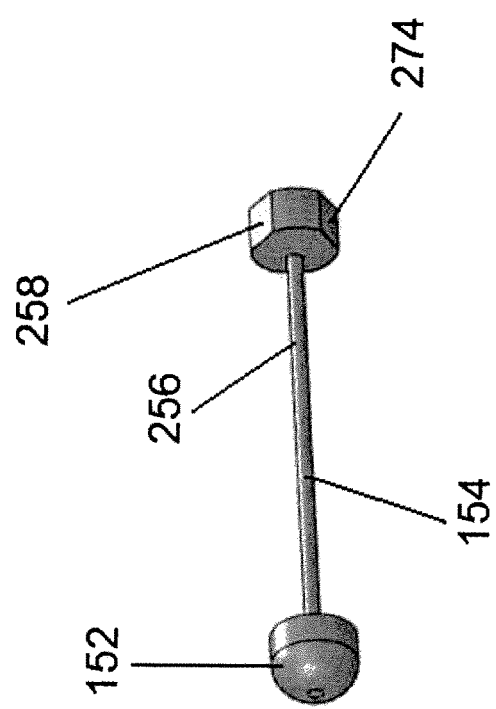
FIG. 10 shows the distal tip and distal core wire of the sensor guide wire of FIGS. 9A and 9B.

To give the sensor element 111 suitable exposure to the surrounding environment so as to obtain readings of the physiological variable of interest, the enlarged portion 158 of the core wire 190 fits within the inner circumference 172 of the circumferential wall 160 of the symmetrical tube 144 so as to block a substantial portion of the passageway into the symmetrical tube 144 with the exception of one or more axial openings 188 along the longitudinal length of the sensor guide wire. The one or more axial openings along the longitudinal length of the sensor guide wire may be formed between the outer circumference 174 of the enlarged portion 158 and the circumferential wall 160 of the symmetrical jacket so as to provide fluid access to the sensor element 111. For example, the enlarged portion 158 may be a circular disc 176 that has been sliced at one side 178, as seen in FIG. 7, or a circular disc 180 that has been sliced at three sides 181, as seen in FIG. 6. Of course, the circular disc may have a slice at only two sides or more than three sides, such as four, five, six or more.

Figure 8:
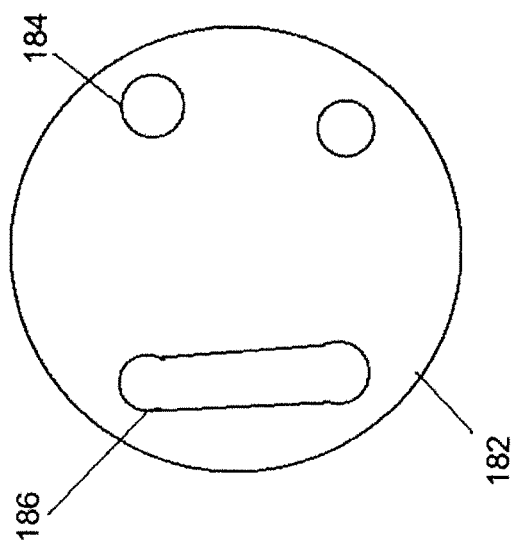
FIG. 8 shows a front view of the enlarged portion of the core wire of FIG. 4 according to another embodiment of the present invention.

According to another embodiment of the present invention, the one or more axial openings may be located within the inner circumference of the enlarged portion 158 whose outer circumference completely engages the inner circumference 172 of the symmetrical jacket. For example, as seen in FIG. 8, the disc 182 may have one, two, three, or more through-holes 184 and/or one, two, three, or more slots 186 running along its longitudinal axis so as to provide one or more axial openings along the longitudinal length of the sensor guide wire so as to provide fluid access to the sensor element 111.

The one or more openings along the longitudinal length of the sensor guide wire provides fluid access to the sensor element 111 so as to impart pressure or fluid contact to the sensor element 111 from fluid that has entered through the spacings of the wire of the coil 142. Thus, the sensor element 111 has exposure to the environmental surroundings without the need to provide an opening or aperture along the circumferential surface of the jacket 144.

FIGS. 9A and 9B show another sensor guide wire 210 that can be used in the system of FIG. 1. The individual elements of this embodiment are the same as the elements of the previous embodiment of FIGS. 1-5 with the exception of the use of the distal core wire 154 and the proximal core wire 140 instead of the use of a single core wire 190.

Figure 11:
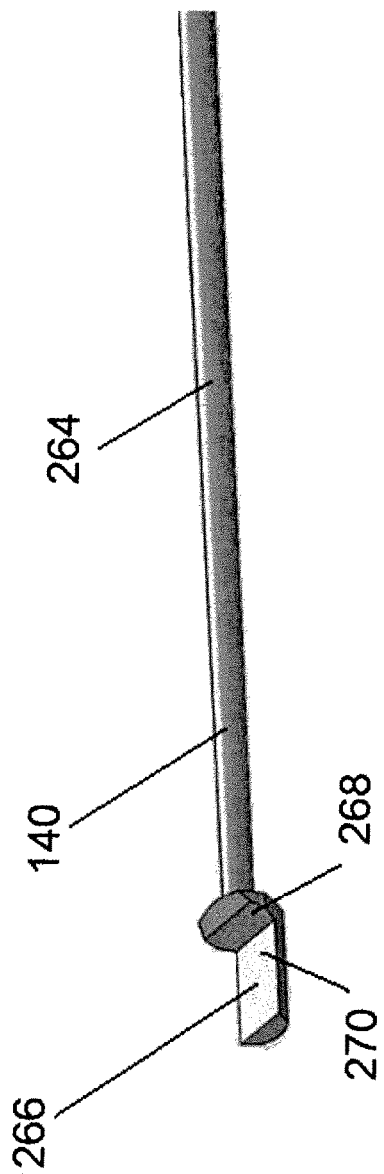
FIG. 11 shows the proximal core wire of the sensor guide wire of FIGS. 9A and 9B.

The proximal core wire 140 is shown in FIG. 11, and may comprise a first body portion 264, and a sensor mounting portion 266. The sensor mounting portion 266 is an enlarged portion of the core wire 140 in which the sensor element 111 is placed on a horizontal flat portion 270 which is connected to the body portion 264 by a connecting portion 268. However, the core wire 140 may have other configurations for mounting the sensor element 111 thereon.

The core wire 154 is a separate core wire from the core wire 140 in that it is spaced from the core wire 140 by a non-zero distance. The core wire 154 comprises a body portion 256 and an enlarged portion 258 at the proximal end of the body portion 256. The enlarged portion 258 and the sensor mounting portion 266 on which the sensor element 111 is mounted are not connected to each other by a bridging portion; however both sections may extend into the jacket 144. The body portion 264, the sensor mounting portion 266, and the connecting portion 268 may be formed as one integral structure fashioned as a unitary one-piece structure or may be two or more distinct components that are connected to each other by suitable attaching mechanisms, for example, laser welding, adhesives, soldering, or other suitable mechanism. Similarly, the body portion 256 and the second enlarged portion 258 may be formed as one integral structure fashioned as a unitary one-piece structure or may be two distinct components that are connected to each other by suitable attaching mechanisms, for example, laser welding, adhesives, soldering, or other suitable mechanism. The core wires 154 and 140 may comprise any suitable material, such as for example, stainless steel or Nitinol.

The arced tip 152 of the distal tip 138 may be connected to the body portion 256 by, for example, laser welding, adhesives, soldering, or other suitable mechanism.

As with the first embodiment, to give the sensor element 111 suitable exposure to the surrounding environment so as to obtain readings of the physiological variable of interest, the enlarged portion 258 of the core wire 154 fits within the inner circumference 172 of the circumferential wall 160 of the symmetrical tube 144 so as to block a substantial portion of the passageway into the symmetrical tube 144 with the exception of one or more axial openings 188 along the longitudinal length of the sensor guide wire. The one or more axial openings along the longitudinal length of the sensor guide wire may be formed between the outer circumference 274 of the enlarged portion 258 and the circumferential wall 160 of the symmetrical jacket so as to provide fluid access to the sensor element 111. For example, the enlarged portion 258 may be a circular disc 176 that has been sliced at one side 178, as seen in FIG. 7, or a circular disc 180 that has been sliced at three sides 181, as seen in FIG. 6. Of course, the circular disc may have a slice at only two sides or more than three sides, such as four, five, six or more. Alternatively or additionally, holes and/or slots may be made on the enlarged portion, as seen in FIG. 8.

FIGS. 12-14 show another sensor guide wire that can be used in the system of FIG. 1. The individual elements of this embodiment are the same as the elements of the previous embodiment of FIGS. 9A-11 with the exception of the addition of a fitting section 360 onto the distal core wire 354.

The core wire 354 comprises a body portion 356 and an enlarged portion 358 at the proximal end of the body portion 356. The enlarged portion 358 and the sensor mounting portion (not shown) on which the sensor element 111 is mounted are not connected to each other by a bridging portion. The fitting section 360 is a section of the core wire onto which the coil 142 fits. Thus, the fitting section 360 secures the coil 142 onto the core wire 354 before being permanently fastened by laser welding, adhesives, or other suitable attaching mechanism.

The body portion 356, the fitting section 360, and the second enlarged portion 358 may be formed as one integral structure fashioned as a unitary one-piece structure or may be two or more distinct components that are connected to each other by suitable attaching mechanisms, for example, laser welding, adhesives, soldering, or other suitable mechanism. The core wire 354 may comprise any suitable material, such as for example, stainless steel or Nitinol.

At location A in FIG. 12, the enlarged portion 358 may be attached to the jacket 144 by any suitable mechanism, such as for example, laser welding, adhesives, soldering, or other suitable mechanism.

The arced tip of the distal tip may be connected to the body portion 356 of the core wire 354, for example, by laser welding, adhesives, soldering, or other suitable mechanism.

As with the first and second embodiments, to give the sensor element 111 suitable exposure to the surrounding environment so as to obtain readings of the physiological variable of interest, the enlarged portion 358 of the core wire 354 fits within the inner circumference of the circumferential wall of the symmetrical tube 144 so as to block a substantial portion of the passageway into the symmetrical tube 144 with the exception of one or more axial openings 388 along the longitudinal length of the sensor guide wire. The one or more axial openings along the longitudinal length of the sensor guide wire may be formed between the outer circumference of the enlarged portion 358 and the circumferential wall of the symmetrical jacket so as to provide fluid access to the sensor element 111. For example, the enlarged portion 358 may be a circular disc 176 that has been sliced at one side 178, as seen in FIG. 7, or a circular disc 180 that has been sliced at three sides 181, as seen in FIG. 6. Of course, the circular disc may have a slice at only two sides or more than three sides, such as four, five, six or more. Alternatively or additionally, holes and/or slots may be made on the enlarged portion, as seen in FIG. 8.

Besides the embodiments above, other embodiments are contemplated. For example, for the sensor wire of FIGS. 2-3 or the sensor wire of FIGS. 9A-9B, the proximal section 150 and the tube section 148; the tube section 148 and the symmetrical jacket 144; or all three of the proximal section 150, the tube section 148, and the symmetrical jacket 144 may be one unified member.

The sensor guide wire may be used to measure any variety of physiological variables, such as blood pressure, blood temperature, blood flow, FFR, or the concentration or presence of one of more blood analytes.

The sensor guide wire may also be used as a guide for a catheter which is pushed over the outer surface of the guide wire.

Besides those embodiments depicted in the figures and described in the above description, other embodiments of the present invention are also contemplated. For example, any single feature of one embodiment of the present invention may be used in any other embodiment of the present invention. For example, the following is a list of embodiments, but the invention should not be viewed as being limited to these embodiments.

(I) A sensor guide wire for an intravascular measurement of a physiological variable in a living body, comprising: a sensor element configured to measure the physiological variable based on exposure to fluid in the living body; and a cylindrical-shaped jacket forming an interior space housing the sensor element, wherein the jacket comprises an outer circumferential wall with a circumferential surface extending between distal and proximal longitudinal ends of the jacket.

(II) The sensor guide wire according to embodiment (I), wherein the outer circumferential wall does not include any apertures along its circumferential surface so as to prevent fluid from passing through the outer circumferential wall.

(III) The sensor guide wire according to any of embodiments (I)-(II), wherein the jacket has a constant cross section along its entire length.

(IV) The sensor guide wire according to any of embodiments (I)-(III), wherein the sensor guide wire comprises one or more axial openings along a longitudinal length of the sensor guide wire that is configured to permit fluid communication between an exterior of the sensor guide wire and the interior space of the jacket.

(V) The sensor guide wire according to any of embodiments (I)-(IV), wherein the one or more axial openings are at least two axial openings.

(VI) The sensor guide wire according to any of embodiments (I)-(IV), wherein the one or more axial openings are at least three axial openings.

(VII) The sensor guide wire according to any of embodiments (I)-(VI), further comprising a coil distal to the jacket, and a core wire with an enlarged portion at the distal longitudinal end of the jacket, and wherein the enlarged portion of the core wire forms the one or more axial openings with the circumferential wall of the jacket.

(VIII) The sensor guide wire according to any of embodiments (I)-(VII), wherein the core wire extends from a distal tip of the sensor guide wire to at least the proximal longitudinal end of the jacket.

(IX) The sensor guide wire according to any of embodiments (I)-(VII), wherein the core wire extends from a distal tip of the sensor guide wire to the distal longitudinal end of the jacket, but does not extend to the sensor element.

(X) The sensor guide wire according to any of embodiments (I)-(IX), further comprising a second core wire that extends from the sensor element to a proximal end of the sensor guide wire.

(XI) The sensor guide wire according to any of embodiments (I)-(X), wherein the jacket is symmetrical along its entire length.

The present invention is not limited to the above-described preferred embodiments. Various alternatives, modifications and equivalents ma be used. Therefore, the above embodiments should not be taken as limiting the scope of the invention.

What is claimed is:

1. A sensor guide wire for an intravascular measurement of a physiological variable in a living body, comprising:
    a sensor element configured to measure the physiological variable based on exposure to fluid in the living body, the sensor element being located in a distal portion of the sensor guide wire that is configured to be inserted into a vessel of the living body;
    a cylindrical jacket forming an interior space housing the sensor element, the jacket having a proximal longitudinal end and a distal longitudinal end opposite the proximal longitudinal end, and the sensor element being located between the proximal longitudinal end of the jacket and the distal longitudinal end of the jacket; and
    a core wire including an enlarged portion at the distal longitudinal end of the jacket,
    wherein the jacket comprises an outer circumferential wall with a circumferential surface extending between the proximal longitudinal end and the distal longitudinal end of the jacket,
    wherein the outer circumferential wall does not include any apertures along its circumferential surface, such that fluid is prevented from passing through the outer circumferential wall, and
    wherein the enlarged portion of the core wire at the distal longitudinal end of the jacket has a shape of a circular disk that is sliced at at least one side, such that the enlarged portion of the core wire includes:
        at least one rounded surface that contacts an inner circumferential surface of the jacket, and
        at least one lateral surface at the at least one sliced side that is spaced from the inner circumferential surface of the jacket so as to form one or more axial openings configured to permit fluid to flow directly from (i) an area distal of the enlarged portion and outside the jacket to (ii) an area proximal of the enlarged portion and inside the jacket such that the fluid contacts a portion of the sensor element that is sensitive to the physiological variable.

2. The sensor guide wire according to claim 1, wherein the jacket has a constant cross section along its entire length.

3. The sensor guide wire according to claim 1, wherein the enlarged portion of the core wire is sliced at two sides, such that the enlarged portion of the core wire includes two rounded surfaces that are rounded and contact an inner circumferential surface of the jacket, and two lateral surfaces at the two sliced sides that are spaced from the inner circumferential surface of the jacket so as to form two axial openings configured to permit fluid communication between an exterior of the sensor guide wire and the interior space of the jacket.

4. The sensor guide wire according to claim 1, wherein the enlarged portion of the core wire is sliced at at least three sides, such that the enlarged portion of the core wire includes at least three rounded surfaces that are rounded and contact an inner circumferential surface of the jacket, and at least three lateral surfaces at the at least three sliced sides that are spaced from the inner circumferential surface of the jacket so as to form at least three axial openings configured to permit fluid communication between an exterior of the sensor guide wire and the interior space of the jacket.

5. The sensor guide wire according to claim 1, further comprising a coil distal to the jacket.

6. The sensor guide wire according to claim 5, wherein the core wire extends from a distal tip of the sensor guide wire to at least the proximal longitudinal end of the jacket.

7. The sensor guide wire according to claim 5, wherein the core wire extends from a distal tip of the sensor guide wire to the distal longitudinal end of the jacket, but does not extend to the sensor element.

8. The sensor guide wire according to claim 7, further comprising a second core wire that extends from the sensor element to a proximal end of the sensor guide wire.

9. The sensor guide wire according to claim 1, wherein the jacket is symmetrical along its entire length.

10. The sensor guide wire according to claim 1, wherein the at least one lateral surface is parallel to an axial direction of the sensor guide wire.

11. The sensor guide wire according to claim 1, wherein a diameter of the enlarged portion is greater than a thickness of the enlarged portion in an axial direction of the sensor guide wire.

12. The sensor guide wire according to claim 1, wherein: the enlarged portion of the core wire includes:
a proximal face at a proximal end of the enlarged portion, the proximal face facing proximally and extending transverse to an axial direction of the core wire, and
a distal face at a distal end of the enlarged portion, the distal face facing distally and extending transverse to the axial direction of the core wire,
the rounded surface that contacts the inner circumferential surface of the jacket extends from the proximal face of the enlarged portion to the distal face of the enlarged portion, and
the at least one lateral surface at the at least one sliced side extends from the proximal face of the enlarged portion to the distal face of the enlarged portion.

13. A sensor guide wire for an intravascular measurement of a physiological variable in a living body, comprising:
a sensor element configured to measure the physiological variable based on exposure to fluid in the living body, the sensor element being located in a distal portion of the sensor guide wire that is configured to be inserted into a vessel of the living body; and
a cylindrical jacket forming an interior space housing the sensor element, the jacket having a proximal longitudinal end and a distal longitudinal end opposite the proximal longitudinal end, and the sensor element being located between the proximal longitudinal end of the jacket and the distal longitudinal end of the jacket; and
a core wire including an enlarged portion at the distal longitudinal end of the jacket,
wherein the jacket comprises an outer circumferential wall with a circumferential surface extending between the proximal longitudinal end and the distal longitudinal end of the jacket,
wherein the enlarged portion of the core wire at the distal longitudinal end of the jacket has a shape of a circular disk that is sliced at at least one side, such that the enlarged portion of the core wire includes:
at least one rounded surface that contacts an inner circumferential surface of the jacket, and
at least one lateral surface at the at least one sliced side that is spaced from the inner circumferential surface of the jacket so as to form one or more axial openings configured to permit fluid to flow directly from (i) an area distal of the enlarged portion and outside the jacket to (ii) an area proximal of the enlarged portion and inside the jacket such that the fluid contacts a portion of the sensor element that is sensitive to the physiological variable.

14. The sensor guide wire according to claim 13, wherein the enlarged portion of the core wire is sliced at two sides, such that the enlarged portion of the core wire includes two rounded surfaces that are rounded and contact an inner circumferential surface of the jacket, and two lateral surfaces at the two sliced sides that are spaced from the inner circumferential surface of the jacket so as to form two axial openings configured to permit fluid communication between an exterior of the sensor guide wire and the interior space of the jacket.

15. The sensor guide wire according to claim 13, further comprising a coil distal to the jacket.

16. The sensor guide wire according to claim 15, wherein the core wire extends from a distal tip of the sensor guide wire to at least the proximal longitudinal end of the jacket.

17. The sensor guide wire according to claim 15, wherein the core wire extends from a distal tip of the sensor guide wire to the distal longitudinal end of the jacket, but does not extend to the sensor element.

18. The sensor guide wire according to claim 17, further comprising a second core wire that extends from the sensor element to a proximal end of the sensor guide wire.

19. The sensor guide wire according to claim 13, wherein the jacket is symmetrical along its entire length.

20. The sensor guide wire according to claim 13, wherein the at least one lateral surface is parallel to an axial direction of the sensor guide wire.

21. The sensor guide wire according to claim 13, wherein a diameter of the enlarged portion in a radial direction of the sensor guide wire is greater than a thickness of the enlarged portion in an axial direction of the sensor guide wire.

22. The sensor guide wire according to claim 13, wherein: the enlarged portion of the core wire includes:
a proximal face at a proximal end of the enlarged portion, the proximal face facing proximally and extending transverse to an axial direction of the core wire, and a distal face at a distal end of the enlarged portion, the distal face facing distally and extending transverse to the axial direction of the core wire, the rounded surface that contacts the inner circumferential surface of the jacket extends from the proximal face of the enlarged portion to the distal face of the enlarged portion, and the at least one lateral surface at the at least one sliced side extends from the proximal face of the enlarged portion to the distal face of the enlarged portion.

\* \* \* \* \*